(12) United States Patent
Schwarzband et al.

(10) Patent No.: US 9,378,923 B2
(45) Date of Patent: *Jun. 28, 2016

(54) THREE-DIMENSIONAL MAPPING USING SCANNING ELECTRON MICROSCOPE IMAGES

(71) Applicant: APPLIED MATERIALS ISRAEL, LTD., Rehovot (IL)

(72) Inventors: Ishai Schwarzband, Yehuda (IL); Yakov Weinberg, Modi-in (IL)

(73) Assignee: Applied Materials Israel, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/609,768

(22) Filed: Jan. 30, 2015

(65) Prior Publication Data
US 2015/0136960 A1 May 21, 2015

Related U.S. Application Data

(63) Continuation of application No. 14/081,981, filed on Nov. 15, 2013, now Pat. No. 8,946,627, which is a continuation of application No. 13/365,238, filed on Feb. 2, 2012, now Pat. No. 8,604,427.

(51) Int. Cl.
H01J 37/00 (2006.01)
H01J 37/24 (2006.01)
(Continued)

(52) U.S. Cl.
CPC .............. H01J 37/24 (2013.01); G01B 21/30 (2013.01); G01D 18/008 (2013.01);
(Continued)

(58) Field of Classification Search
CPC ............... H01J 2237/22; H01J 2237/2448; H01J 2237/2814; H01J 37/244
USPC ........... 250/307, 306, 310, 397, 252.1, 492.2, 250/492.3; 257/48
See application file for complete search history.

(56) References Cited

U.S. PATENT DOCUMENTS 4,485,873 A * 12/1984 Balzer ................... C09K 8/584
166/400
6,429,427 B1 * 8/2002 Frosien ................. H01J 37/268
250/306
(Continued)

OTHER PUBLICATIONS

Marinello et al., "Critical Factors in SEM 3D Stereo Microscopy," Measurement Science and Technology, vol. 19, No. 06, year 2008, pp. 1-13.
(Continued)

Primary Examiner — Phillip A Johnston
(74) Attorney, Agent, or Firm — Lowenstein Sandler LLP

(57) ABSTRACT

A method includes irradiating a surface of a sample, which is made-up of multiple types of materials, with a beam of primary electrons. Emitted electrons emitted from the irradiated sample are detected using multiple detectors that are positioned at respective different positions relative to the sample, so as to produce respective detector outputs. Calibration factors are computed to compensate for variations in emitted electron yield among the types of the materials, by identifying, for each material type, one or more horizontal regions on the surface that are made-up of the material type, and computing a calibration factor for the material type based on at least one of the detector outputs at the identified horizontal regions. The calibration factors are applied to the detector outputs. A three-dimensional topographical model of the surface is calculated based on the detector outputs to which the calibration factors are applied.

20 Claims, 5 Drawing Sheets

(51) Int. Cl.
*H01J 37/244* (2006.01)
*H01J 37/28* (2006.01)
*G01B 21/30* (2006.01)
*G01D 18/00* (2006.01)
*H01J 37/26* (2006.01)
*G01N 23/225* (2006.01)

(52) U.S. Cl.
CPC .............. *H01J 37/244* (2013.01); *H01J 37/26* (2013.01); *H01J 37/28* (2013.01); *G01N 23/2251* (2013.01); *G01N 2223/6116* (2013.01); *H01J 2237/22* (2013.01); *H01J 2237/2448* (2013.01); *H01J 2237/24465* (2013.01); *H01J 2237/2814* (2013.01); *H01J 2237/2826* (2013.01)

(56) References Cited

U.S. PATENT DOCUMENTS

| | | | |
|---|---|---|---|
| 6,573,498 B1 | 6/2003 | Rangarajan et al. | |
| 6,930,308 B1 | 8/2005 | Lorusso et al. | |
| 7,005,641 B2* | 2/2006 | Nakasuji | B82Y 10/00 250/310 |
| 7,067,808 B2 | 6/2006 | Kochi et al. | |
| 7,705,304 B2 | 4/2010 | Kawamata et al. | |
| 7,875,850 B2* | 1/2011 | Nakayama et al. | 250/310 |
| 8,405,045 B2* | 3/2013 | Preikszas et al. | 250/396 R |
| 8,604,427 B2* | 12/2013 | Schwarzband et al. | 250/306 |
| 8,946,627 B2* | 2/2015 | Schwarzband et al. | 250/306 |

OTHER PUBLICATIONS

Maurer, William, "To Share and to Learn", Bacus News, vol. 27, Issue 2, Feb. 2011, pp. 1-5.

Frankot, et al., "A Method for Enforcing Integrability in Shape from Shading Algorithms," IEEE Transactions on Pattern Analysis and Machine Intelligence, vol. 10., No. 4, Jul. 1988, pp. 439-451.

Harada, et al., "A New CDSEM Metrology Method for Thin Film Hardmasks Patterns using Multiple Detectors," Photomask Japan, Yokohama, Apr. 13-15, 2010 (published in Bacus News, vol. 27, issue 2, Feb. 2011).

USPTO Non-Final Office Action dated May 15, 2014, U.S. Appl. No. 14/081,981 filed Nov. 15, 2013.

USPTO Notice of Allowance dated Sep. 26, 2014, U.S. Appl. No. 14/081,981 filed Nov. 15, 2013.

USPTO Notice of Allowance dated Aug. 8, 2013, U.S. Appl. No. 13/365,238 filed Feb. 2, 2012.

* cited by examiner

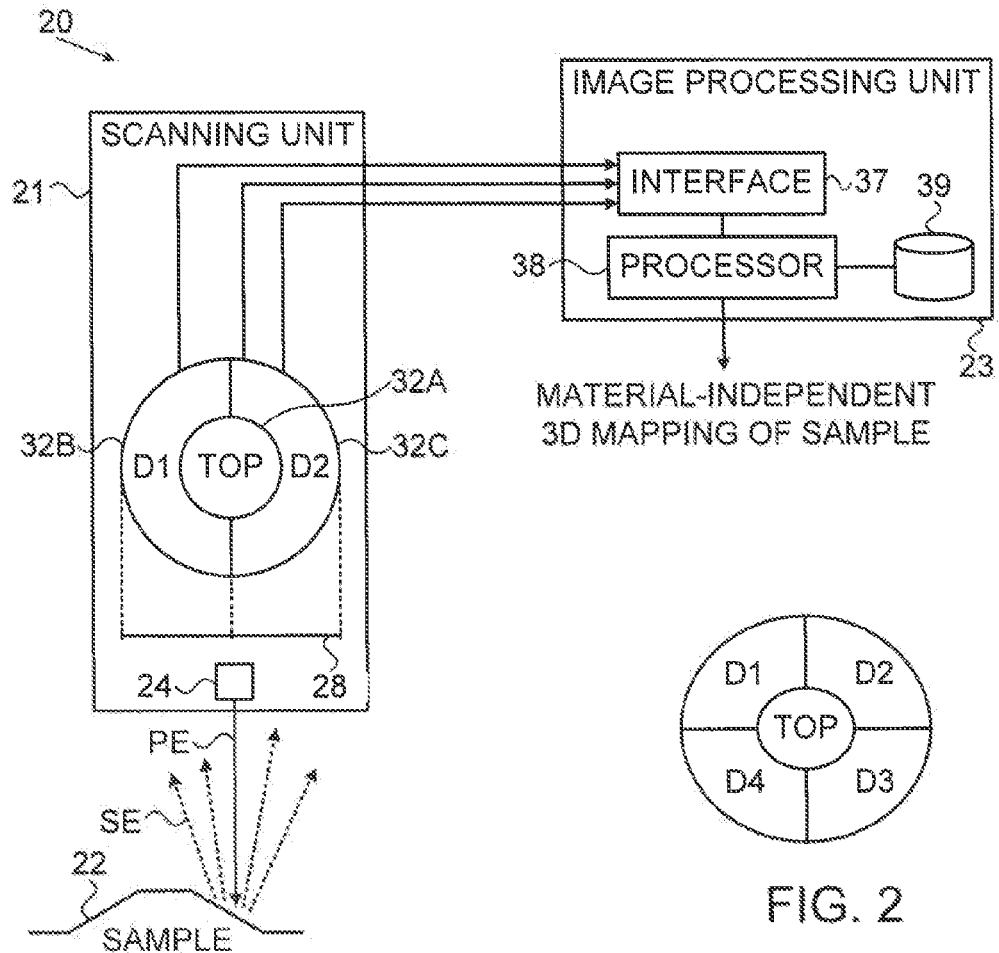
FIG. 1
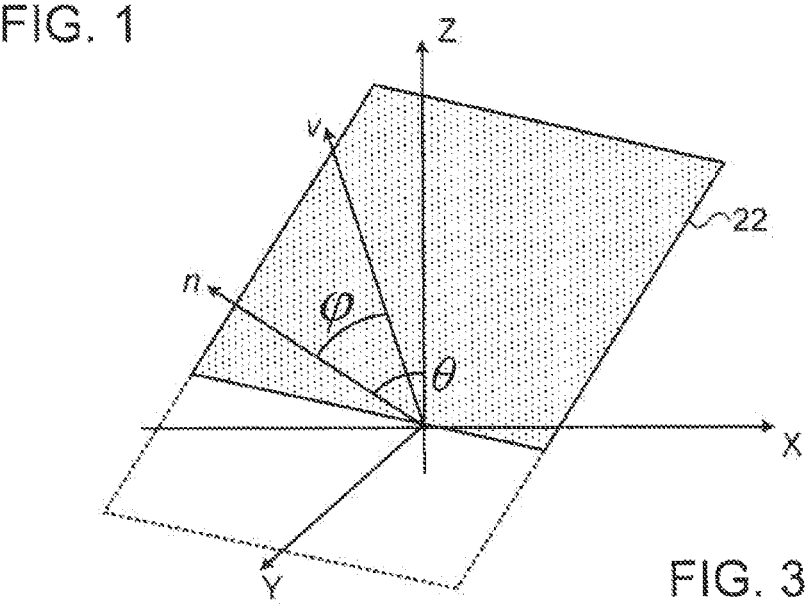
FIG. 2
FIG. 3

THREE-DIMENSIONAL MAPPING USING SCANNING ELECTRON MICROSCOPE IMAGES

RELATED APPLICATIONS

This patent application is a continuation of U.S. patent application Ser. No. 14/081,981 filed on Nov. 15, 2013, which is a continuation of U.S. patent application Ser. No. 13/365,238 filed on Feb. 2, 2012, now U.S. Pat. No. 8,604,427, all of which are incorporated by reference herein.

TECHNICAL FIELD

Embodiments of the present invention relates generally to processing of Scanning Electron Microscope (SEM) images, and particularly to methods and systems for three-dimensional mapping using SEM images.

BACKGROUND

Scanning Electron Microscope (SEM) images are used in various mapping and imaging applications, such as for inspection of semiconductor wafers. Several techniques are known in the art for three-dimensional (3D) mapping of samples using SEM images. For example, a conventional technique for inspecting semiconductor devices utilizes multiple sets of measurement data obtained by a SEM to determine the dimensional parameters of a semiconductor device. The SEM collects each set of data from a different angular orientation with respect to the device. The dimensional parameters of the semiconductor device are determined by analyzing the relationship between the SEM inspection angle and the collected data sets.

Another conventional method includes a 3D shape measurement in which detection signals from respective semiconductor elements are sequentially switched in synchronization with a scanning frame of an electron beam on a sample. The detection signals from the respective semiconductor elements can be sequentially recorded in recording addresses in a frame memory that correspond to the respective semiconductor elements. After four electron beam scanning sessions, each image data for 3D shape measurement is recorded in the frame memory, and processed for 3D shape measurement.

As yet another example, Marinello et al., describes dimensional measurements performed with a SEM using 3D reconstruction of surface topography through stereo-photogrammetry, in "Critical Factors in SEM 3D Stereo Microscopy," Measurement Science and Technology, volume 19, no. 6, 2008, which is incorporated herein by reference.

Some conventional SEM mapping techniques use multiple detectors. For example, Harada et al. describe multi-detector SEM measurements in "A New CDSEM Metrology Method for Thin Film Hardmasks Patterns using Multiple Detectors," Photomask Japan 2010 (published in BACUS News 27:2, February, 2011).

SUMMARY

A method includes irradiating a surface of a sample, which is made-up of multiple types of materials, with a beam of primary electrons. Emitted electrons emitted from the irradiated sample are detected using multiple detectors that are positioned at respective different positions relative to the sample, so as to produce respective detector outputs. Calibration factors are computed to compensate for variations in emitted electron yield among the types of the materials, by identifying, for each material type, one or more horizontal regions on the surface that are made-up of the material type, and computing a calibration factor for the material type based on at least one of the detector outputs at the identified horizontal regions. The calibration factors are applied to the detector outputs. A three-dimensional topographical model of the surface is calculated based on the detector outputs to which the calibration factors are applied.

In some embodiments, the detectors include a top detector that is positioned perpendicularly above a plane of the sample, and two or more side detectors that are positioned at oblique angles relative to the plane of the sample. In an embodiment, identifying the horizontal regions includes segmenting the surface into multiple segments made-up of the respective types of the materials, and identifying one or more of the horizontal regions within each of the segments.

In one embodiment, calculating the three-dimensional topographical model includes estimating height gradients at multiple points on the surface, and integrating the height gradients to produce the three-dimensional topographical model. Estimating the height gradients may include defining, for a given point on the surface, a set of equations that express the detector outputs as a function of respective reflectance functions, and deriving a height gradient at the given point by solving the set of the equations. In an embodiment, the method includes evaluating a reflectance function of a given detector by integrating an angular distribution of the emitted electron yield over a range of angles captured by the given detector. Estimating the height gradients may include resolving an ambiguity in a component of the height gradients by applying a criterion that requires an integral of the height gradients over a closed loop path on the surface to be zero.

In some embodiments, applying the calibration factors includes normalizing a reflectance function for a given detector, which is estimated at a point on the surface that is made-up of a material type, using a calibration factor computed for the material type. In an embodiment, the detectors include a top detector positioned perpendicularly above a plane of the sample, and four side detectors positioned at oblique angles relative to the plane of the sample, detecting the emitted electrons includes combining the detector outputs of selected pairs of the side detectors, and calculating the three-dimensional topographical model includes computing the model based on the combined detector outputs.

There is additionally provided, in accordance with an embodiment of the present invention, an apparatus including an electron source, multiple detectors and a processor. The electron source is configured to irradiate a surface of a sample, which is made-up of multiple types of materials, with a beam of primary electrons. The detectors are positioned at respective different positions relative to the sample and are configured to detect emitted electrons that are emitted from the irradiated sample, so as to produce respective detector outputs. The processor is configured to compute calibration factors to compensate for variations in emitted electron yield among the types of the materials by identifying, for each material type, one or more horizontal regions on the surface that are made-up of the material type, and computing a calibration factor for the material type based on at least one of the detector outputs at the identified horizontal regions, to apply the calibration factors to the detector outputs, and to calculate a three-dimensional topographical model of the surface based on the detector outputs to which the calibration factors are applied.

There is also provided, in accordance with an embodiment of the present invention, an apparatus including an interface and a processor. The interface is configured to receive multiple detector outputs from respective detectors positioned at respective different positions relative to a sample, which is made-up of multiple types of materials, wherein the detector outputs are indicative of emitted electrons that are emitted from the sample in response to irradiation of the sample by a beam of primary electrons. The processor is configured to compute calibration factors to compensate for variations in emitted electron yield among the types of the materials by identifying, for each material type, one or more horizontal regions on the surface that are made-up of the material type, and computing a calibration factor for the material type based on at least one of the detector outputs at the identified horizontal regions, to apply the calibration factors to the detector outputs, and to calculate a three-dimensional topographical model of the surface based on the detector outputs to which the calibration factors are applied.

There is further provided, in accordance with an embodiment of the present invention, a computer software product, the product including a tangible non-transitory computer-readable medium, in which program instructions are stored, which instructions, when read by a computer, cause the computer to receive multiple detector outputs from respective detectors positioned at respective different positions relative to a sample, which is made-up of multiple types of materials, wherein the detector outputs are indicative of emitted electrons that are emitted from the sample in response to irradiation of the sample by a beam of primary electrons, to compute calibration factors to compensate for variations in emitted electron yield among the types of the materials by identifying, for each material type, one or more horizontal regions on the surface that are made-up of the material type, and computing a calibration factor for the material type based on at least one of the detector outputs at the identified horizontal regions, to apply the calibration factors to the detector outputs, and to calculate a three-dimensional topographical model of the surface based on the detector outputs to which the calibration factors are applied.

BRIEF DESCRIPTION OF THE DRAWINGS

The present invention will be more fully understood from the following detailed description of the embodiments thereof, taken together with the drawings in which:

FIG. 1 is a block diagram that schematically illustrates a system for three-dimensional (3D) mapping of samples, in accordance with an embodiment of the present invention;

FIG. 2 is a diagram that schematically illustrates a detector array, in accordance with an alternative embodiment of the present invention;

FIGS. 3 and 4 are diagrams showing geometrical conventions used in describing embodiments of the present invention;

DETAILED DESCRIPTION

Overview

Figure 4:
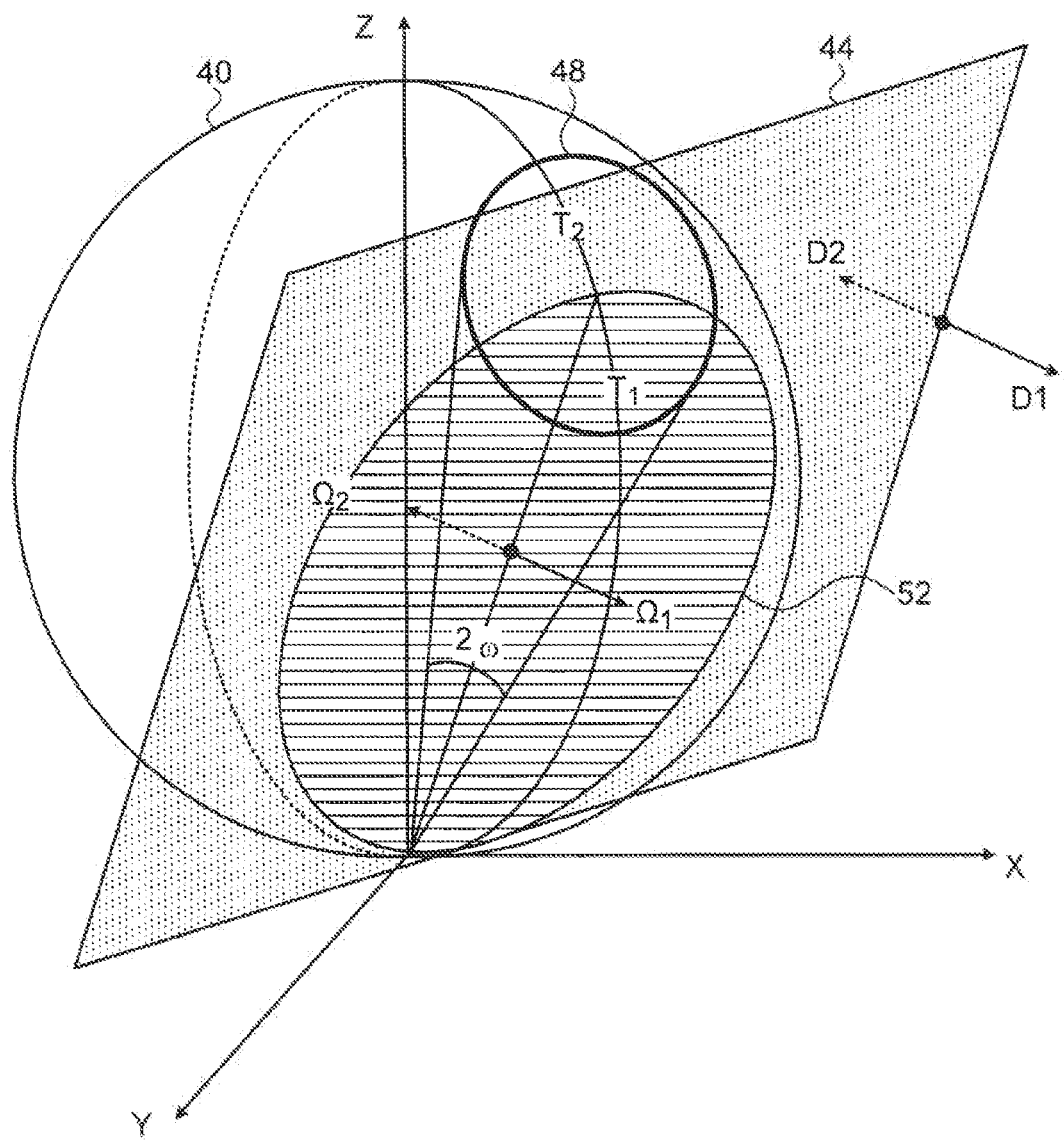

Embodiments of the present invention provide methods and systems for calculating a three-dimensional (3D) topographical model of a sample surface from multiple Scanning Electron Microscope (SEM) images of the sample, captured by multiple detectors. In particular, a disclosed calibration process prevents distortion of the 3D model when the sample surface is made-up of multiple types of materials.

In some embodiments, the sample is irradiated with a beam of primary electrons. Multiple detectors, which are positioned at different positions relative to the sample, detect secondary and backscattered electrons that are emitted from the irradiated sample. For example, the detectors may comprise a top detector that is positioned directly above the sample, plus two or more side detectors.

Each detector produces a respective detector output that is indicative of the yield of secondary electrons captured by the detector. A processor reconstructs a 3D topographical model of the sample by processing the multiple detector outputs. Typically, the processor estimates surface height gradients across the sample, and then integrates the gradients to produce the 3D topographical model.

In many practical applications, the sample surface is made-up of multiple types of materials. Unless accounted for, the differences in material types may distort the 3D reconstruction, because the yield of secondary electrons in a particular direction depends not only on the surface topography but also on its material composition.

In one embodiment, the processor computes calibration factors to compensate for the variations in secondary electron yield among the different material types. The processor applies the calibration factors to the detector outputs in calculating the 3D topographical model of the surface. In an example embodiment, the processor identifies, for each material type, one or more regions of the surface that are substantially horizontal. The processor performs reference yield measurements for the different material types at the horizontal regions, and uses these measurements to compute the calibration factors. The processor then applies these calibration factors to the outputs of the detectors, produced in other regions of the sample. As a result, the 3D topographical model is unaffected by the different material types of the sample surface.

The methods and systems described herein produce highly-accurate 3D models of samples, irrespective of the various material types that may be present on the sample surface. The disclosed techniques can be used in a variety of applications that examine samples having multiple materials, such as in Critical Dimension (CD) measurements, Defect Review (DR) and Automatic Defect Classification (ADC) of semiconductor wafers.

System Description

FIG. 1 is a block diagram that schematically illustrates a Scanning Electron Microscope (SEM) system 20 for three-dimensional (3D) mapping, in accordance with an embodiment of the present invention. In the present example, system 20 comprises a scanning unit 21 composed of, inter-alia, a SEM column system (not shown), detection system (not shown) and a handling system (not shown) for handling samples, scanning the samples using SEM and detecting signals indicative of, e.g., the shape, design, material and other features of the samples.

System 20 further comprises an image processing unit 23 that processes digital images that are produced by detectors in scanning unit 21. As will be explained below, however, this sort of partitioning is not mandatory, and the functions of system 20 can be implemented in a single unit or partitioned among multiple units as appropriate.

System 20 can be used in various applications, such as in Critical Dimension (CD) metrology, Defect Review (DR) or any other suitable application. In the embodiments described herein, the samples mapped by system 20 comprise semiconductor wafers. Alternatively, however, system 20 can be used for 3D mapping of any other suitable type of sample, such as semiconductor masks and reticles, flat display panels, solar panels and more.

Scanning unit 21 in system 20 scans a sample 22, which has a certain height profile or surface topography. For example, the sample may comprise a patterned semiconductor wafer on which electronic components, conductors and other elements are disposed. Unit 21 irradiates sample 22 using a beam of electrons, detects secondary electrons that are emitted from the sample in response to the irradiation, and uses the secondary electron detection to generate a 3D model of the sample surface using methods that are described in detail below.

Unit 21 in the present example comprises an electron source 24, which irradiates sample 22 with a beam of Primary Electrons (PE). Typically, the PE beam irradiates a certain point on the sample surface at any given time, and the beam scans the sample, e.g., in a raster pattern. In response to irradiation by the PE, Secondary Electrons (SE) are emitted from the irradiated point on the sample. The SE are emitted in various angles and are detected by a detector array 28.

Figure 7:
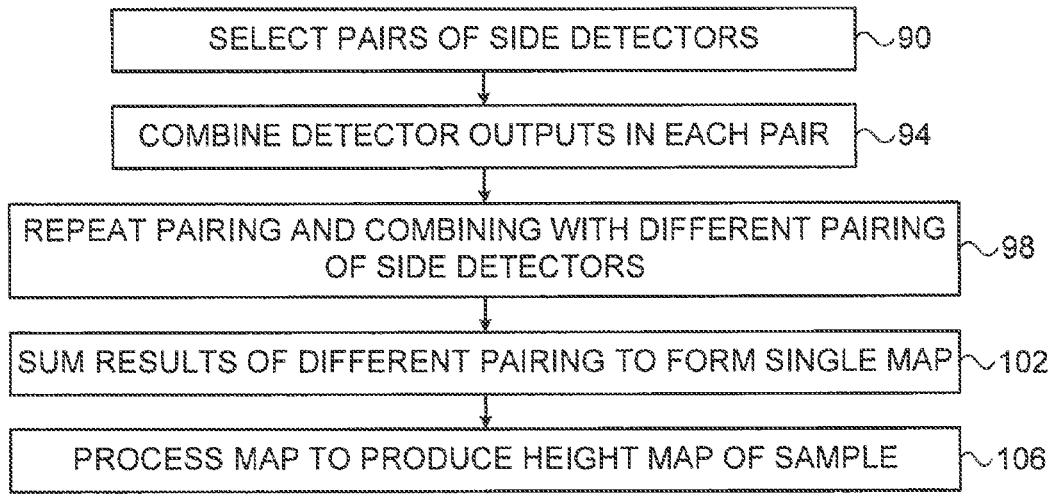

In the present embodiment, array 28 comprises a top detector 32A and two side detectors 32B and 32C respectively denoted D1 and D2. The top detector is positioned perpendicularly above the plane of the sample, whereas the side detectors are positioned at oblique angles relative to the sample plane. An alternative detector configuration having four side detectors is shown in FIG. 2 below. An example technique of manipulating the outputs of the four side detectors is shown in FIG. 7 below. (Sample 22, electron source 24 and array 28 are shown in the figure in a side view. The configuration of detectors 32A . . . 32C in array 28, however, is shown in a top view for the sake of clarity.)

Each detector captures the SE in a certain range of angles relative to the irradiation point. In the example of FIG. 1, top detector 32A captures the SE that are emitted within a certain conical sector whose vertex is the irradiation point. Each of side detectors 32B and 32C captures the SE in a respective, different angular and energy sector.

Typically, the top detector is used for segmenting the image of the sample surface into regions of different material compositions, as will be explained further below. The top detector is best suited for this task since it is highly sensitive to material contrast, as opposed to the side detectors that are more sensitive to topography contrast. Unlike oblique collection of SE, in normal collection of SE (as performed by the top detector) each point in the collected image is accurately indicative of a single irradiated point of the sample surface and less affected by contributions from the surroundings of the irradiated point.

Thus, when analyzing the output of the top detector, intensity differences that are not associated with edges of patterns are typically indicative of material composition differences. The disclosed techniques thus generate material-related information and use this information for the generation of a 3D model, e.g., height map, of a sample. The material-related information is generated by processing signals produced by the top detector. Edge information is typically disregarded when performing material segmentation. Nevertheless, in alternative embodiments, the top detector may also be used for other purposes.

In one example embodiment, electron source 24 comprises an electron gun, and each of detectors 32A . . . 32C comprises a combination of a scintillator and a Photo-Multiplier Tube (PMT). Detector array 28 is positioned e.g. 120 mm above the sample, the diameter of top detector 32A is e.g. on the order of 14 mm, and the external diameter of side detectors 32B and 32C is e.g. on the order of 25 mm. These implementation details are given, however, purely by way of example. In alternative embodiments any other suitable configuration can be used. Typically, each detector captures the SE in a certain respective range of angles and energies, determined by the geometry.

Each detector generates a signal that depends on the yield of secondary electrons within the angular sector captured by the detector. As the PE beam scans the sample, each detector generates a signal that depends, as a function of time, on the SE yield within its respective angular sector from the currently-irradiated point on the sample.

In the example of FIG. 1, image processing unit 23 produces a 3D model (e.g., height map) of the surface of sample 22, based on the signals generated by detectors 32A . . . 32C. Unit 23 comprises an interface 37 that receives the signals produced by the detectors, and a processor 38 that carries out the mapping methods described herein. In particular, processor 38 calibrates the signals produced by the detectors such that the 3D model is unaffected by differences in material composition of the sample surface. Although the embodiments described herein refer mainly to sample surfaces having two different material types, the disclosed techniques can be used for mapping samples whose surfaces are made-up of any desired number of material types.

In some embodiments, unit 23 comprises a storage device 39 for storing digital representations of the detector outputs, the resulting height map, and/or any other suitable information. Typically, processor 38 comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

FIG. 2 is a diagram that schematically illustrates a detector array, in accordance with an alternative embodiment of the present invention. In the present example, the array comprises a top detector and four quadrant side detectors denoted D1 . . . D4. The array of FIG. 2 can be used instead of array 28 in system 20. Further alternatively, system 20 may comprise any other suitable number of detectors arranged in any other suitable geometrical configuration. An example method of manipulating the outputs of detectors D1 . . . D4 is described in FIG. 7 below.

The system configuration of FIG. 1 above is an example configuration. In alternative embodiments, system 20 can be implemented in any other suitable configuration. For example, the disclosed embodiments refer to configurations having two or four side detectors. The disclosed techniques, however, are not limited to such configurations, and alternative embodiments may use any other suitable number of side detectors.

As another example, the disclosed techniques may be performed "on-tool," i.e., by image processing unit 23 of system 20. In these embodiments, processor 38 carries out the disclosed mapping techniques, possibly along with other image processing functions of system 20. In alternative embodiments, the disclosed techniques can be carried out by a separate, dedicated system or processor. System elements that are not mandatory for understanding of the disclosed techniques have been omitted from the figure for the sake of clarity.

Geometrical Conventions

FIG. 3 is a diagram showing the geometrical conventions that are used in the subsequent description. The particular geometrical notation used herein is in no way limiting, and is used purely for the sake of conceptual clarity.

Sample 22 is positioned in a certain plane relative to the x, y and z axes. A vector n marks the normal to this plane. In other words, vector n is perpendicular to sample 22. The inclination of the sample with respect to the x-y plane, i.e., the angle between n and the z axis, is denoted θ. The origin of the coordinate system (x=y=z=0) marks the point at which the sample is irradiated with the PE beam at a given time. The beam irradiates the sample along the z axis, from top to bottom.

As a result of the irradiation, SE are emitted from the sample in various directions. The yield y of SE depends on the tilt angle θ, typically in accordance with y=y(cos(θ)). The velocity vectors of the SE, denoted v, are typically distributed in accordance with Lambert's law, i.e., $p \propto \cos(\phi)$, wherein $\phi$ denotes the angle between v and n.

3D Reconstruction of Height Profile Based on Multiple Detector Signals

Let H denote the height profile of sample 22, i.e., the height of the wafer surface as a function of location on the wafer. The signal level produced by the ith detector, denoted Ei, depends on the gradient of the height profile, and on the relative direction between the detector and the irradiation point. We can write:

$$E_i = k_i \cdot Y_0 \cdot R_i(\bar{g}, \{\bar{d}_1, \bar{d}_2, \ldots\}) \quad [1]$$

wherein $\bar{g}$ denotes the gradient of the height profile $\bar{g}=\nabla H$, and $\bar{d}_l$ denotes the vector from the irradiation point to the $l^{th}$ detector. $R_i$ denotes a reflectance function, $Y_0$ denotes the total SE yield from a horizontal surface, and k denotes a machine-dependent constant.

For the case of two side detectors, the signals produced by the detectors for a given irradiation point can be written as:

$$E_1 = E_1(\bar{g}, \bar{d}_1, \bar{d}_2), E_2 = E_2(\bar{g}, \bar{d}_1, \bar{d}_2) \quad [2]$$

Once measured values of E1 and E2 are available from the detectors, this equation system can be solved to derive the two components of the height gradient $\bar{g}$ at the irradiation point. For a different number of detectors, a similar equation system can be defined and solved.

In some embodiments, processor 38 accepts the measured signal levels Ei from the detectors, and solves equation system [2] to derive the height gradient $\bar{g}$. System 20 repeats this process for multiple irradiation points on sample 22, so as to produce a height gradient map of the sample. Then, processor 38 reconstructs the height profile H of the sample from the height gradient map, by implementing any suitable reconstruction method. Typically, processor 38 reconstructs the height profile by integrating the height gradient map in two dimensions.

The reflectance function $R_i$ of the $i^{th}$ detector can be written as:

$$R_i(\bar{g}, \bar{d}) = Y(|\bar{g}|) \cdot \eta_i(\bar{g}, \bar{d}_1, \bar{d}_2) \quad [3]$$

wherein y denotes the total relative SE yield, and ηi denotes the fraction of SE captured by the ith detector. The term $y(|\bar{g}|)$ in Equation [3] is common to all detectors. The terms $\eta_i(\bar{g}, \bar{d}_1, \bar{d}_2)$ indicate the relative distribution of captured SE among the different detectors.

In various embodiments, processor 38 may use various known models of dependency of y on θ. In one example embodiment, processor 38 uses an inverse cosine dependence, i.e., y=1/cos θ. In another embodiment, processor 38 uses the dependence $y=(\cos \theta)^{-\alpha}$. In yet another embodiment, processor 38 uses the dependence $y=(\xi-\cos\theta)/[1+(\xi-2)\cdot\cos\theta]$. Further alternatively, processor 38 may use any other suitable dependence of y on θ. Since y=y(cos(θ)), the term $y(|\bar{g}|)$ can be written as $y(|\bar{g}|)=y(\sqrt{1+|\bar{g}|^2})$.

In some embodiments, processor 38 computes each ii term in the reflectance function of Equation [3] by integrating the Lambert distribution function over the angular sector (in φ/ψ polar coordinates) captured by the ith detector.

FIG. 4 is a diagram showing the geometrical notation used in integrating the Lambert distribution function, in accordance with an example embodiment of the present invention. In this representation, a plane 44 passes through the origin (the irradiation point) and is positioned symmetrically with respect to detectors D1 and D2. In other words, plane 44 passes through the origin and is orthogonal to the line connecting detectors D1 and D2. The subspace that falls on the same side of plane 44 as detector D1 is marked Ω1, and the subspace that falls on the same side of plane 44 as detector D2 is marked Ω2.

A contour 40 marks the Lambertian that represents the spatial distribution of secondary electron yield. A contour 52 marks the intersection of Lambertian 40 and plane 44. Angle 2ω denotes the apex angle of the conical sector that is captured by top detector 32A, i.e., a fixed physical property of system 20. A contour 48 marks a dome that is defined by the intersection of this conical sector and Lambertian 40. The part of dome 48 that falls on the D1 side of plane 44 is denoted T1, and the part of dome 48 that falls on the D2 side of plane 44 is denoted T2.

As can be seen from these definitions, integrating the Lambert distribution function over the dome (i.e., over the interior of contour 48) gives the secondary electron yield that is captured by the top detector. Thus, η1 and η2 can be written as:

$$\eta_1 = \int\int_{\Omega_1 - T_1} \sin\varphi\cos\varphi \cdot d\varphi d\psi \quad [4]$$

$$\eta_2 = \int\int_{\Omega_2 - T_2} \sin\varphi\cos\varphi \cdot d\varphi d\psi$$

Typically, processor 38 calculates the integrals of Equation [4] numerically, since there are usually no closed-forms expressions for these integrals. Having calculated the reflectance function Ri of Equation [3] above, processor 38 may solve Equation [3] to derive the height gradient map $\bar{g}$.

Calibration of 3D Mapping to Account for Surface Material

Up to this point, the above-described process did not take into account differences in material composition across the surface of sample 22. In many practical scenarios, however, the surface of sample 22 comprises different features or structures that are made of different materials. For example, some regions of the surface may comprise substrate material such as Silicon, while other regions may comprise metallic conductors, other semiconductor materials or any other suitable material.

As can be appreciated, the yield of secondary electrons in a particular direction depends both on the height gradient and on the material composition at the irradiation point. Consequently, signals $E_i$ produced by the detectors of system 20 depend on these two factors, as well. Unless accounted for, differences in material composition may distort the estimation of the height gradient map $\bar{g}$, and therefore distort the 3D model of the sample calculated by system 20.

In some embodiments of the present invention, processor 38 carries out a calibration process that factors-out the material composition of the sample surface. The disclosed calibration process distinguishes between the two factors affecting the SE yield—surface topography and surface material. When using this calibration process, the resulting 3D model of sample 22 is substantially unaffected by material composition differences, and therefore better reproduces the sample surface topography.

The signal produced by the ith detector, Ei, is defined by Equation [1] above. The term $R_i(\bar{g}, \{\bar{d}_1, \bar{d}_2,\})$ in Equation [1] depends only on the surface topography. When the sample surface comprises different materials, however, the term $k_i \cdot Y_0$ in Equation [1] is unknown a-priori, and may vary from one irradiation point to another, since Y0 depends on the type of material.

In some embodiments, processor 38 solves this problem by calibrating the reflectance function Ri for a given irradiation point to account for the actual material at that point. For a perfectly horizontal plane, we can write:

$$y=1, \eta_i = \eta_H \quad [5]$$

wherein ηH denotes the fraction of SE captured from a horizontal plane—a constant that depends on the detector geometry. The signal produced by the ith detector in response to irradiating a horizontal plane is thus given by:

$$E_{iH} = k_i \cdot Y_0 \cdot \eta_H \quad [6]$$

Processor 38 may obtain EiH, for example, by choosing a reference irradiation point on sample 22 that is known to be horizontal ($\bar{g}=0$), and measuring the detector signals when this point is irradiated. Having obtained $E_{iH}$, processor 38 may derive $k_i \cdot Y_0$ from Equation [6]. This derivation gives the value of $k_i \cdot Y_0$ for the specific material at the reference (horizontal) irradiation point. Thus, the process of choosing reference irradiation points in the images and deriving $E_{iH}$ should typically be repeated for each type of material that is present on the sample surface.

When later measuring a given irradiation point, processor 38 normalizes the reflectance function Ri with the EiH value that is applicable to the type of material at the given irradiation point:

$$R_i = \frac{E_i}{E_{iH}} \cdot \eta_H \quad [7]$$

Since both Ei and EiH depend on the type of material, the normalized Ri depends only on surface topography and not on material. From the normalized reflectance functions $R_i$, processor 38 is able to derive the height gradient $\bar{g}$ at the irradiation point. This derived value of $\bar{g}$ is independent of material type. The description that follows explains an example scheme of deriving $\bar{g}$ from $R_i$.

Thus, in the present context, the measured reference EiH values for the different material types are regarded as calibration factors that processor 38 applies to the detector outputs in computing the 3D topographical model of the sample surface.

In alternative embodiment, processor 38 may compute and apply any other suitable kind of calibration factors that compensate for the differences in secondary electron yield of different materials.

It can be shown that Ri can be written as:

$$R_i = y(|\bar{g}|) \cdot \eta_i(\gamma) \quad [8]$$

wherein γ is defined by:

$$\gamma \equiv \cos(\angle \bar{n}, \Delta \bar{d}) = \frac{(\bar{g} \cdot \Delta \bar{d})}{\sqrt{1+|\bar{g}|^2}} \quad [9]$$

wherein $\bar{n}$ denotes a unit vector that is normal (perpendicular) to the sample surface at the irradiation point, and $\Delta \bar{d}$ denotes a unit vector along the line connecting the two side detectors. The term $(\bar{g} \cdot \Delta \bar{d})$ denotes a scalar product of the two vectors.

It can be shown that the gradient $\bar{g}$ is given by:

$$|\bar{g}| = y^{-1}\left(\frac{R_1}{V_1(r_{12})}\right), (\bar{g}, \Delta \bar{d}) = F^{-1}(r_{12}) \cdot \sqrt{1+|\bar{g}|^2} \quad [10]$$

wherein $$r_{11} = \frac{R_1}{R_2} = \frac{\eta_1(\gamma)}{\eta_2(\gamma)} \equiv F(\gamma) \Rightarrow \gamma = F^{-1}(r_{12}) \quad [11]$$

$$R_1 = y(|\bar{g}|) \cdot \eta_1(F^{-1}(r_{12})) = y(|\bar{g}|) \cdot V_1(r_{12}) \quad [12]$$

In some embodiments, processor 38 calculates the two components of $\bar{g}$ from Equation [10]. The functions F-1 and V1 depend on ω (the apex angle of the conical sector captured by the top detector). Typically, processor 38 holds predefined tables of values of these functions, and uses the tables to evaluate the functions when calculating $\bar{g}$.

Figure 5:
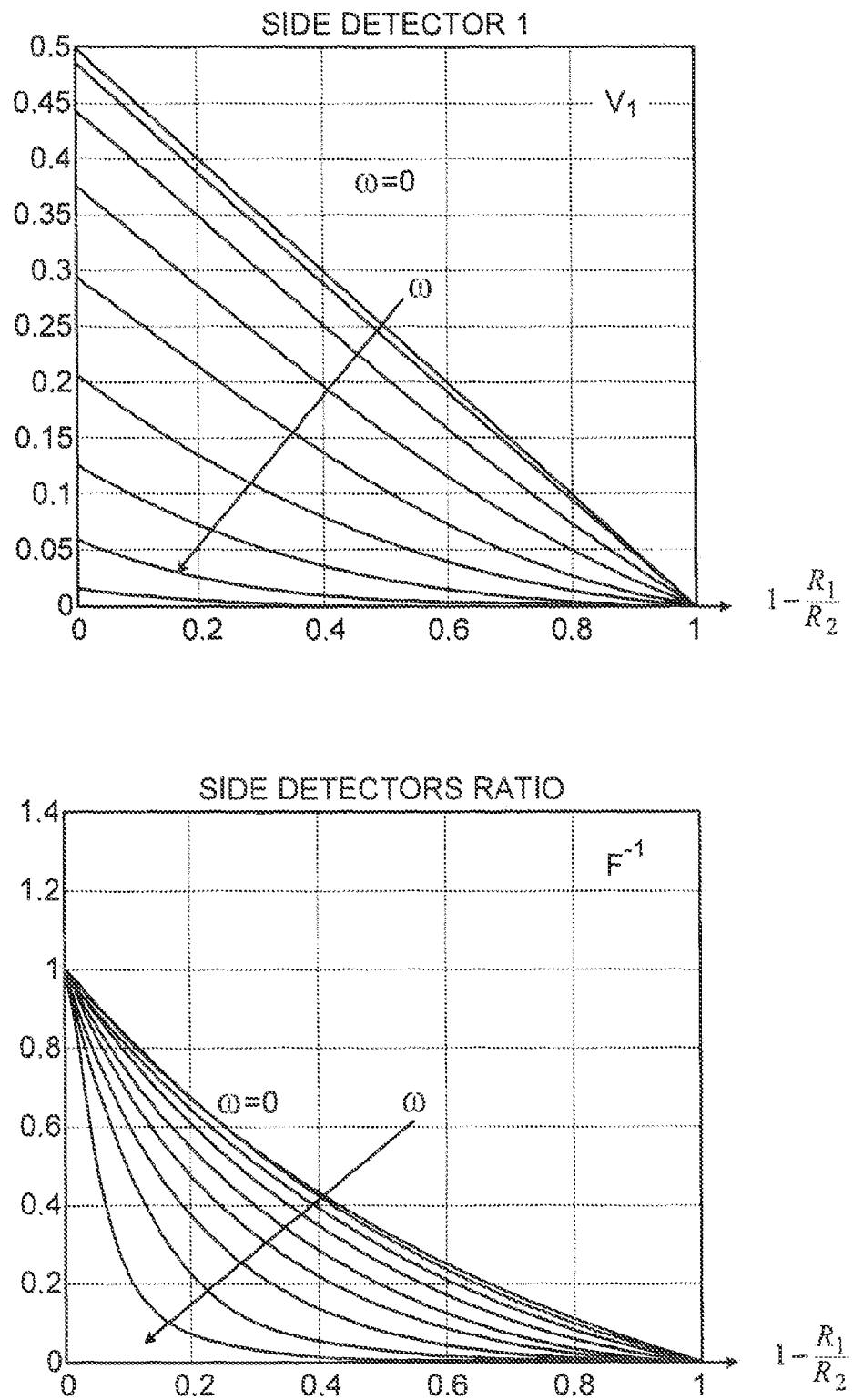
FIG. 5 is a graph showing functions used in calculating a height gradient map, in accordance with an embodiment of the present invention.

FIG. 5 is a graph showing functions F-1 and V1 used in calculating a height gradient map, in accordance with an example embodiment of the present invention. The top graph in the figure shows function V1 for various values of ω, and the bottom graph shows function F-1 for different values of w. In alternative embodiments, e.g., for other detector geometries, any other suitable functions can be used.

In some embodiments, processor 38 calculates one component of the height gradient $\bar{g}$ that is along the line connecting the two side detectors D1 and D2, and another component of the gradient that is perpendicular to this line. The two components are denoted $g_d$ and $g_{d\perp}$, respectively, and are given by:

$$g_d = (\bar{g} \cdot \Delta \bar{d}), g_{d\perp} = \pm \sqrt{|\bar{g}|^2 - g_d^2} \quad [13]$$

Note that the perpendicular gradient component $g_{d\perp}$ is ambiguous, i.e., has two solutions that are theoretically possible. One possible way to resolve this ambiguity is to use the integrability property of gradient functions. Generally, the integral of a gradient function over a closed loop is zero:

$$C = \oint_S (\bar{g} \cdot d\bar{s}) = 0 \quad [14]$$

wherein S may denote any closed loop path on the sample surface. By choosing a rectangular path with two sides parallel with $g_d$ and two sides parallel with $g_{d\perp}$, the requirement of Equation [14] can be written as:

$$C = \int g_d \cdot dy - \int g_{d\perp} \cdot dx = 0 \quad [15]$$

From Equation [15] it can be seen that $$\int g_d \cdot dy > 0 \Rightarrow g_{d\perp} > 0 \quad [16]$$

In some embodiments, processor 38 tests both hypotheses (both the positive value and the negative values of $g_{d\perp}$ in Equation [13]) in the test of Equations [15] and [16]. The hypothesis for which the integral of Equation [15] is closer to zero is chosen as the correct value of $g_{d\perp}$.

The above-described ambiguity resolution test may not function properly when the height profile slope is parallel to the line connecting detectors D1 and D2. One possible solution is to position sample 22 such that its features are oriented obliquely relative to the line connecting the detectors. In an example embodiment, the sample is placed such that its axes are at a 45° angle (in the x-y plane) relative to the line connecting the detectors.

After computing the two components of gradient $\bar{g}$ at each irradiation point on the sample surface, processor 38 integrates the gradient in two dimensions to reconstruct the height map H of the sample. In practice, however, the computed gradient components may not be readily integrable, because they are often approximate and deviate from an ideal gradient function. Thus, the task of integrating the gradient can be regarded as the task of finding a two-dimensional scalar map whose two-dimensional gradient is as close as possible to the computed gradient. In some embodiments, processor 38 finds such a scalar map and outputs it as the reconstructed height map of the sample.

Various methods for fitting a scalar map to a given gradient map are known in the art, and any such method can be used by processor 38. An example method is described by Frankot and Chellappa, in "A Method for Enforcing Integrability in Shape from Shading Algorithms," IEEE Transactions on Pattern Analysis and Machine Intelligence, Volume 10, No. 4, July, 1988, pages 439-451. According to this article, the height map is calculated by:

$$F_H(\omega) = \frac{-j\omega_x F_{gx} - j\omega_y F_{gy}}{\omega_x^2 + \omega_y^2} \quad [17]$$

wherein $F_H(\omega)$ denotes the Fourier transform of the height map H, and $F_{gx}$ and $F_{gy}$ denote the Fourier transforms of the gradient components.

3D Mapping Method Description

Figure 6:
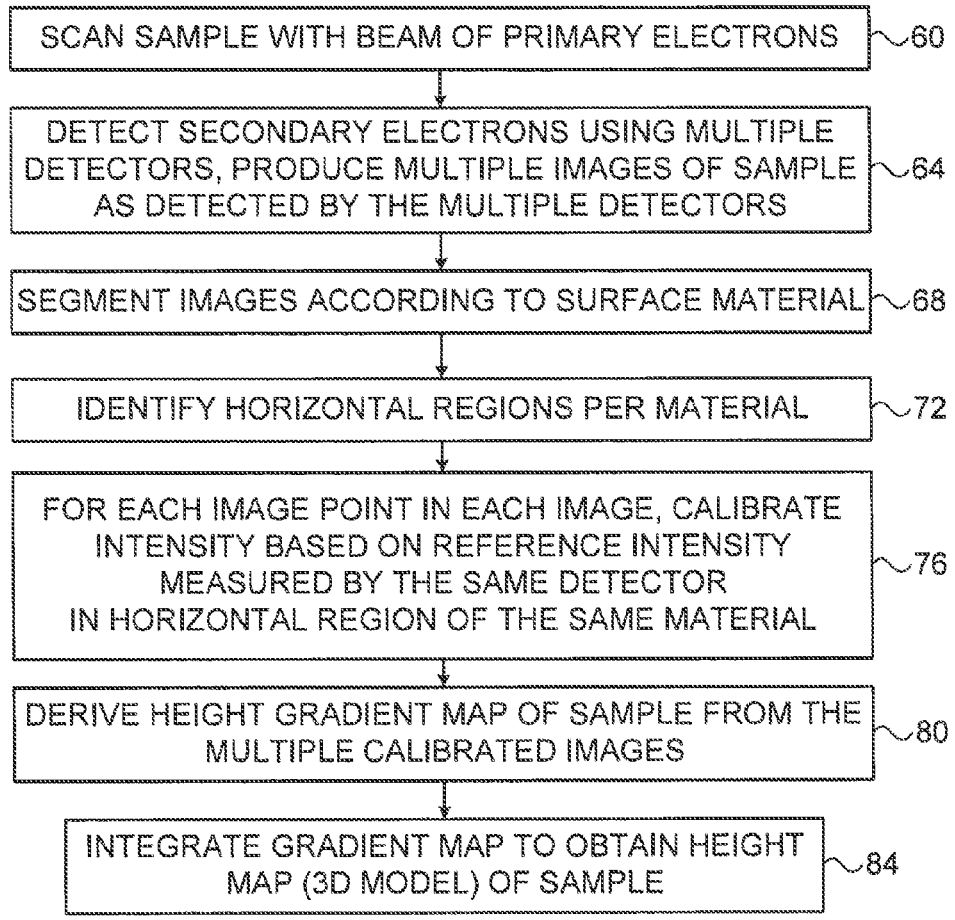
FIGS. 6 and 7 are flow charts that schematically illustrate methods for 3D mapping of samples, in accordance with embodiments of the present invention.

FIG. 6 is a flow chart that schematically illustrates a method for 3D mapping of a sample, e.g. wafer sample 22 shown in FIG. 1, carried out by an inspection, metrology or review system, e.g. system 20 shown in FIG. 1, in accordance with an embodiment of the present invention. The method begins with system 20 scanning sample 22 with a beam of Primary Electrons (PE), at a scanning step 60. During the scan, detectors 32A . . . 32C detect the Secondary Electrons (SE) that are emitted from the sample for each irradiated point on the sample surface, at a detection step 64. Digital representations of the detector signals are provided to processor 38 of mapping unit 36 via interface 37.

Processor 38 produces multiple SEM images of the sample, one image per each detector. The image of a given detector comprises a two-dimensional array of values that indicate the SE yield captured by that detector from the various irradiated points on the sample surface. In the example configuration of FIG. 1, processor 38 produces three images corresponding to detectors 32A . . . 32C (the top detector plus two side detectors). Processor 38 uses these images to calculate the 3D height map of sample 22, taking into account and compensating for the types of material making up the sample surface.

In some embodiments, processor 38 divides the sample surface into segments depending on the surface material, at a segmentation step 68. Each segment comprises the points on the sample surface that are made-up of a respective material. For example, one segment may comprise the locations on the sample surface that are made-up of Silicon, and another segment may comprise the locations on the sample surface that are made-up of metal conductors. Processor 38 may use any suitable image processing scheme for carrying out this segmentation. The processor may perform the segmentation based on any single image or based on multiple images. In one embodiment, the processor uses the image of top detector 32A for this purpose.

For each type of material, processor 38 identifies one or more regions on the sample surface that are substantially horizontal, at a region identification step 72. Processor 38 may identify the horizontal regions in various ways. In an example embodiment, most of the sample surface is horizontal, with the exception of feature edges that can be detected by processing one or more of the SEM images produced by the detectors. Processor 38 may identify edges in one of the images, and segment the image using the identified edges. The processor may differentiate between horizontal regions made of different materials based on the measured electron yield in each segment. Typically, although not necessarily, the processor uses the image of top detector 32A for this purpose.

For each type of material, processor 38 uses one or more points in the horizontal regions of this material to estimate EiH, as explained above with respect to Equation [6]. The processor stores the estimated EiH of each material type for later use in calibration.

For each irradiated point on the sample surface, processor 38 calculates the gradient $\bar{g}$ of the height map based on the corresponding image points in the multiple images. In some embodiments, processor 38 calculates the reflectance functions Ri and calibrates them so as to factor out the type of material using the pre-calculated EiH values, at a reflectance calculation step 76. Processor 38 may calculate the reflectance functions for a given irradiation point by: (i) identifying the type of material at the given irradiation point, and (ii) normalizing the reflectance functions Ri for the given irradiation point using the EiH value of the identified material type.

Processor 38 then calculates the gradient map $\bar{g}$ from the normalized reflectance functions Ri, at a gradient calculation step 80. The calculation may follow, for example, the process of Equations [8]-[13] above. At this stage, processor 38 has a gradient map of the sample that is unaffected by the different material types. Processor 38 now derives the height map H of the sample from the gradient map, at a height map derivation step 84. The derivation may follow, for example, the process of Equations [14]-[17] above. The height map is then provided as output. In some embodiments the height map can be presented to an operator using a suitable Graphical User Interface (GUI). Additionally or alternatively, the height map can be provided to another system or application for subsequent processing, e.g., for measuring Critical Dimensions (CD) of the sample or for Defect Review (DR).

The embodiments described herein refer to calibration of the signals produced by the multiple detectors in order to factor-out the effect of the multiple materials making up the sample surface. In alternative embodiments, however, the disclosed calibration schemes can be applied to any suitable direct or indirect output of the detectors, such as to the images produced by processor 38 from the detector signals.

FIG. 7 is a flow chart that schematically illustrates a method for 3D mapping of a sample, in accordance with an alternative embodiment of the present invention. The method of FIG. 7 is used in conjunction with the four side detector configuration of FIG. 2 above. In the present example, the method begins with processor 38 selecting pairs of side detectors, at a pairing step 90. Typically, the processor selects pairs of adjacent side detectors, e.g., D1+D2 and D3+D4.

Processor 38 combines the outputs (images) produced by the side detectors in each pair, at a pair combining step 94. In an embodiment, processor 38 repeats the pairing and combining process for different pairs of side detectors, at a re-pairing step 98. For example, processor 38 may initially (step 90) pair detectors D1+D2 and D3+D4, and subsequently (step 98) pair detectors D1+D4 and D2+D3.

Processor 38 sums the results of the two pairing operations, at a summation step 102, to form a single composite image. Processor 38 then processes this single image to produce a 3D height map of the sample, at a processing step 106. This processing may use, for example, the method of FIG. 6 above.

Figure 8:
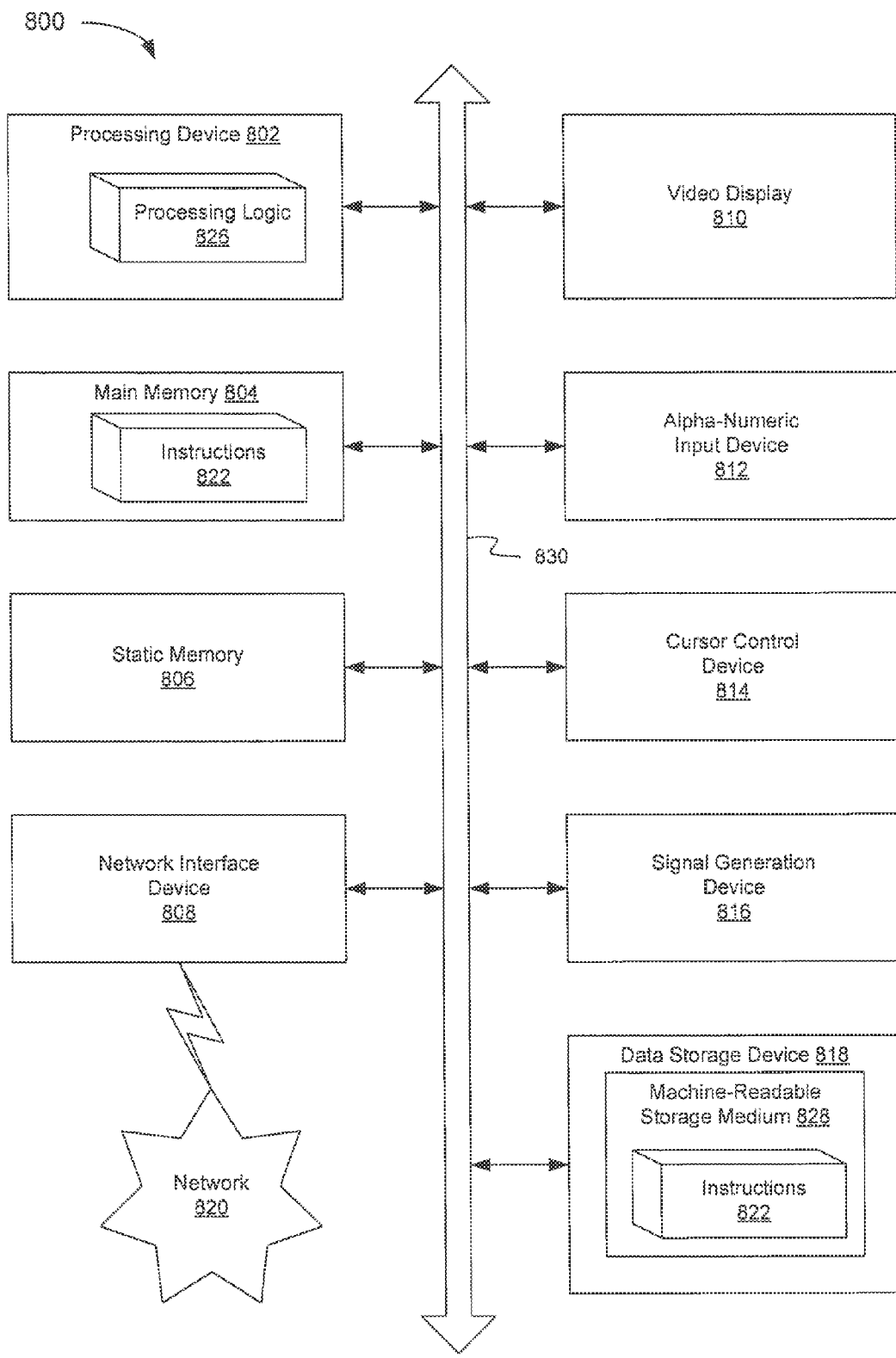
FIG. 8 is a block diagram illustrating one embodiment of a computer system, according to an embodiment.

FIG. 8 illustrates a diagrammatic representation of a machine in the exemplary form of a computer system 800 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 800 may be representative of a server, such as server 102, running image converter 110.

The exemplary computer system 800 includes a processing device 802, a main memory 804 (e.g., read-only memory (ROM), flash memory, dynamic random access memory (DRAM) (such as synchronous DRAM (SDRAM) or Rambus DRAM (RDRAM), etc.), a static memory 806 (e.g., flash memory, static random access memory (SRAM), etc.), and a data storage device 818, which communicate with each other via a bus 830. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 802 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. The processing device 802 is configured to execute processing logic 826 for performing the operations and steps discussed herein.

The computer system 800 may further include a network interface device 808. The computer system 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 816 (e.g., a speaker).

The data storage device 818 may include a machine-readable storage medium 828, on which is stored one or more set of instructions 822 (e.g., software) embodying any one or more of the methodologies of functions described herein. The instructions 822 may also reside, completely or at least partially, within the main memory 804 and/or within the processing device 802 during execution thereof by the computer system 800; the main memory 804 and the processing device 802 also constituting machine-readable storage media. The instructions 822 may further be transmitted or received over a network 820 via the network interface device 808.

While the machine-readable storage medium 828 is shown in an exemplary embodiment to be a single medium, the term "machine-readable storage medium" should be taken to include a single medium or multiple media (e.g., a centralized or distributed database, and/or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the scope of the present invention.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

Although the embodiments described herein mainly address inspection of semiconductor wafers, the methods and systems described herein can also be used in other applications, such as in inspection of masks.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method comprising:
receiving information corresponding to a detection of electrons emitted from an irradiated surface of a sample comprising a plurality of types of materials;
computing calibration factors to compensate for a variation in a yield of the electrons emitted among the plurality of types of materials of the sample; and
calculating, by a processing device, a three-dimensional (3D) model of the surface of the sample based on the received information corresponding to the detection of electrons emitted from the irradiated surface of the sample and the calibration factors to compensate for the variation in the yield of the electrons emitted among the plurality of types of materials of the sample.

2. The method of claim 1, wherein the information corresponding to the detection of electrons emitted corresponds to a plurality of detector outputs that are associated with different positions relative to the irradiated surface of the sample.

3. The method of claim 1, wherein the calculating of the 3D model of the surface of the sample comprises:
generating a surface height gradient of the surface of the sample; and
integrating the surface height gradient.

4. The method of claim 1, wherein the generating of the surface height gradient of the surface of the sample comprises:
defining, for a given point on the surface of the sample, a set of equations corresponding to reflectance functions; and
deriving a corresponding surface height gradient at the given point by solving the set of the equations.

5. The method of claim 1, wherein the calculating of the 3D model comprises:
applying the calibration factors to the information corresponding to the detection of electrons emitted from the irradiated surface of the sample to compensate for the plurality of types of materials of the sample.

6. The method of claim 5, wherein applying the calibration factors comprises normalizing a reflectance function for a given detector associated with the detection of electrons emitted corresponding to a point on the surface of the material that comprises a material type by using a particular calibration factor of the calibration factors that is computed for the material type.

7. The method of claim 1, wherein the information corresponding to the detection of electrons emitted from the irradiated surface of the sample comprises at least one Scanning Electron Microscope (SEM) image.

8. A system comprising:
a memory; and
a processing device operatively coupled with the memory to:
receive information corresponding to a detection of electrons emitted from an irradiated surface of a sample comprising a plurality of types of materials;
compute calibration factors to compensate for a variation in a yield of the electrons emitted among the plurality of types of materials of the sample; and
calculate a three-dimensional (3D) model of the surface of the sample based on the received information corresponding to the detection of electrons emitted from the irradiated surface of the sample and the calibration factors to compensate for the variation in the yield of the electrons emitted among the plurality of types of materials of the sample.

9. The system of claim 8, wherein the information corresponding to the detection of electrons emitted corresponds to a plurality of detector outputs that are associated with different positions relative to the irradiated surface of the sample.

10. The system of claim 8, wherein the calculating of the 3D model of the surface of the sample comprises:
generating a surface height gradient of the surface of the sample; and
integrating the surface height gradient.

11. The system of claim 8, wherein the generating of the surface height gradient of the surface of the sample comprises:
defining, for a given point on the surface of the sample, a set of equations corresponding to reflectance functions; and
deriving a corresponding surface height gradient at the given point by solving the set of the equations.

12. The system of claim 8, wherein the calculating of the 3D model comprises:
applying the calibration factors to the information corresponding to the detection of electrons emitted from the irradiated surface of the sample to compensate for the plurality of types of materials of the sample.

13. The system of claim 12, wherein applying the calibration factors comprises normalizing a reflectance function for a given detector associated with the detection of electrons emitted corresponding to a point on the surface of the material that comprises a material type by using a particular calibration factor of the calibration factors that is computed for the material type.

14. The system of claim 8, wherein the information corresponding to the detection of electrons emitted from the irradiated surface of the sample comprises at least one Scanning Electron Microscope (SEM) image.

15. A non-transitory machine-readable storage medium having data that, when accessed by a processing device, cause the processing device to:
receive information corresponding to a detection of electrons emitted from an irradiated surface of a sample comprising a plurality of types of materials;
compute calibration factors to compensate for a variation in a yield of the electrons emitted among the plurality of types of materials of the sample; and calculate, by the processing device, a three-dimensional (3D) model of the surface of the sample based on the received information corresponding to the detection of electrons emitted from the irradiated surface of the sample and the calibration factors to compensate for the variation in the yield of the electrons emitted among the plurality of types of materials of the sample.

16. The non-transitory machine-readable storage medium of claim 15, wherein the information corresponding to the detection of electrons emitted corresponds to a plurality of detector outputs that are associated with different positions relative to the irradiated surface of the sample.

17. The non-transitory machine-readable storage medium of claim 15, wherein the calculating of the 3D model of the surface of the sample comprises:

generating a surface height gradient of the surface of the sample; and integrating the surface height gradient.

18. The non-transitory machine-readable storage medium of claim 15, wherein the generating of the surface height gradient of the surface of the sample comprises:

defining, for a given point on the surface of the sample, a set of equations corresponding to reflectance functions; and deriving a corresponding surface height gradient at the given point by solving the set of the equations.

19. The non-transitory machine-readable storage medium of claim 15, wherein the calculating of the 3D model comprises:

applying the calibration factors to the information corresponding to the detection of electrons emitted from the irradiated surface of the sample to compensate for the plurality of types of materials of the sample.

20. The non-transitory machine-readable storage medium of claim 19, wherein applying the calibration factors comprises normalizing a reflectance function for a given detector associated with the detection of electrons emitted corresponding to a point on the surface of the material that comprises a material type by using a particular calibration factor of the calibration factors that is computed for the material type.

* * * * *